United States Patent
Jain et al.

(10) Patent No.: US 9,408,806 B2
(45) Date of Patent: *Aug. 9, 2016

(54) TABLET DOSAGE FORM

(71) Applicants: Girish Kumar Jain, Delhi (IN);
Ramakant Gundu, Ahmednagar (IN);
Rahul Dabre, Nagpur (IN)

(72) Inventors: Girish Kumar Jain, Delhi (IN);
Ramakant Gundu, Ahmednagar (IN);
Rahul Dabre, Nagpur (IN)

(73) Assignee: Wockhardt Limited, Bandra East, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 14/026,106

(22) Filed: Sep. 13, 2013

(65) Prior Publication Data

US 2015/0079170 A1 Mar. 19, 2015
US 2016/0213620 A9 Jul. 28, 2016

Related U.S. Application Data

(63) Continuation of application No. 12/602,168, filed as application No. PCT/IB2008/051092 on Mar. 25, 2008, now Pat. No. 8,574,625.

(30) Foreign Application Priority Data

May 30, 2007 (IN) .................................... 1006/2007
Mar. 19, 2008 (IN) .................................... 558/2008

(51) Int. Cl.
| *A61K 9/28* | (2006.01) |
| *A61K 31/40* | (2006.01) |
| *A61K 31/4184* | (2006.01) |
| *A61K 31/4418* | (2006.01) |
| *A61K 31/55* | (2006.01) |
| *A61K 45/06* | (2006.01) |
| *A61K 31/196* | (2006.01) |
| *A61K 31/4422* | (2006.01) |
| *A61K 31/5575* | (2006.01) |

(52) U.S. Cl.
CPC .............. *A61K 9/2886* (2013.01); *A61K 31/196* (2013.01); *A61K 31/40* (2013.01); *A61K 31/4184* (2013.01); *A61K 31/4418* (2013.01); *A61K 31/4422* (2013.01); *A61K 31/55* (2013.01); *A61K 31/5575* (2013.01); *A61K 45/06* (2013.01)

(58) Field of Classification Search
None
See application file for complete search history.

(56) References Cited

U.S. PATENT DOCUMENTS 7,871,643 B2 * 1/2011 Lizio et al. ..................... 424/452
2005/0222136 A1 * 10/2005 Buschmann et al. ......... 514/221

FOREIGN PATENT DOCUMENTS

| EP | 1020182 | * | 1/2000 | ............... A61K 9/20 |
| WO | WO 00/01368 | * | 1/2000 | ............... A61K 9/26 |

* cited by examiner

*Primary Examiner* — Jake Vu
(74) *Attorney, Agent, or Firm* — Bio Intellectual Property Services LLC (Bio IPS); O. (Sam) Zaghmout

(57) ABSTRACT

The present invention relates to novel tablet dosage forms and methods of preparing these forms, which can be used for different classes of pharmaceutical active ingredients posing stability issues in a single unit system. The dosage form includes a first layer, which includes a tablet of one or more active pharmaceutical ingredients, which is inlayed in the first layer along with other pharmaceutically acceptable excipients, and a second layer that includes one or more active pharmaceutical ingredients optionally with other pharmaceutically acceptable excipients.

9 Claims, 2 Drawing Sheets

FIG. 1G

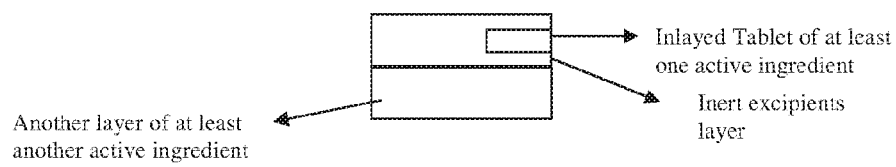

Inlayed Tablet of at least one active ingredient

Inert excipients layer

Another layer of at least another active ingredient

FIG. 1H

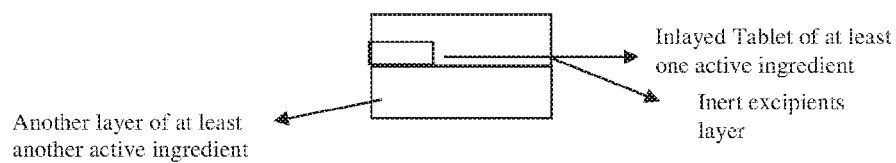

Inlayed Tablet of at least one active ingredient

Inert excipients layer

Another layer of at least another active ingredient

FIG. 1I

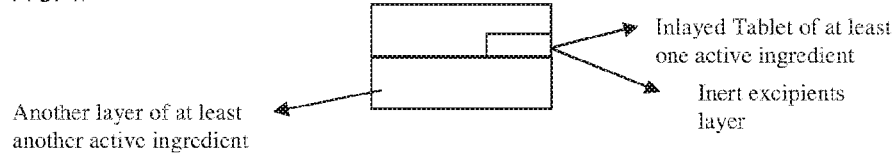

Inlayed Tablet of at least one active ingredient

Inert excipients layer

Another layer of at least another active ingredient

TABLET DOSAGE FORM

CROSS REFERENCE TO RELATED APPLICATIONS

This application is a Continuation of application Ser. No. 12/602,168, filed Jan. 18, 2010, now pending, which claims benefit of PCT/IB2008/051092, filed Mar. 25, 2008; 558/MUM/2008 (India), filed Mar. 19, 2008; and 1006/MUM/2007 (India), filed May 30, 2007. The entire disclosure of these prior applications are hereby incorporated by reference.

FIELD OF THE INVENTION

The present invention relates to novel tablet dosage forms and methods of preparing these forms, which can be used for different classes of pharmaceutical active ingredients posing stability issues in a single unit system. The dosage form includes a first layer that includes a tablet of one or more active pharmaceutical ingredients, which is inlayed in the first layer along with other pharmaceutically acceptable excipients, and a second layer that includes one or more active pharmaceutical ingredients optionally with other pharmaceutically acceptable excipients.

BACKGROUND OF THE INVENTION

There is an ever-increasing desire for combining active ingredients belonging to different therapeutic categories. However, instability of the active ingredients poses a major obstacle in combining these active ingredients in a single dosage form. Drug instability is the phenomenon, which occurs when the effects of one drug are modified by the presence of another drug in the same dosage form. Therefore, combination dosage form which combines the features of pharmacologic efficacy, adequate drug stability, and a reliable and robust method of manufacture has to overcome a number of technical problems to be formulated in a single dosage form. Further, the standard approach of directly mixing the active ingredients with the necessary excipients cannot be applied to combination products of different active ingredients and more sophisticated techniques are needed to separate the different active ingredients in a single dosage form.

There are various types of combination products dosage forms conceivable but it cannot be predicted which of these dosage forms best combines product stability, pharmacological efficacy, and a reliable manufacturing method. It is an object of the present invention to provide a novel tablet dosage form, which can encompass drugs of different classes which otherwise pose stability issues in a single unit.

There are several references known in the literature, which describe different techniques/methods/dosage forms combining different drugs in one unit dosage form.

International Publication No. (PCT) WO 2007/043061 discloses a tablet-in-tablet system wherein two chemically incompatible anti-malarial compounds are separated by a film coating.

European Patent Application No. EP1216030A1 discloses a dosage form including a mixture of a delay release formulation of a non-steroidal anti-inflammatory drug (NSAID) and a mixture containing a prostaglandin and one or more excipients.

European Patent Application No. EP1091731 discloses a dosage form that includes a non-steroidal anti-inflammatory drug (NSAID) in coated pellets and misoprostol is located outside the pellets in the form of a solid dispersion in hydroxypropyl methylcellulose or polyvinylpyrrolidone.

U.S. Pat. Nos. 5,601,843 and 5,698,225 disclose a tablet having a core of a NSAID selected from diclofenac and piroxicam, which core is surrounded by a mantle coating of a prostaglandin such as misoprostol, wherein an intermediate coating can be present between the NSAID core and prostaglandin mantle coating.

U.S. Pat. No. 5,015,481 describes compositions that include an admixture of an NSAID selected from diclofenac and piroxicam, a prostaglandin such as misoprostol, and a stabilizer, preferably hydroxypropyl methylcellulose.

U.S. Pat. Nos. 6,183,779 and 6,287,600 disclose a dosage form that includes an NSAID present in enteric-coated granules or particles and misoprostol is located outside the pellets in the form of a solid dispersion in hydroxypropyl methylcellulose or polyvinylpyrrolidone. U.S. Pat. Nos. 6,387,410; 6,514,525; 6,537,582 and 6,787,155 disclose a similar dosage form that includes the NSAID containing pellets in a delayed release formulation.

U.S. Pat. No. 5,232,704 discloses a capsule dosage form containing one layer that includes a drug release layer containing misoprostol and the other a buoyant or floating layer.

U.S. Application No. 2005163847 discloses a solid dosage form that includes a first portion comprising NSAID; and a coating containing an antiulcerative compound, said coating at least partially surrounding the NSAID portion.

Non-steroidal anti-inflammatory drugs (NSAIDs) present a great therapeutic benefit in the treatment of inflammatory conditions such as arthritis, but have an ulcerogenic effect in the upper gastrointestinal tract, which can seriously limit their usefulness, especially for chronic treatment. Certain prostaglandin type compounds, especially prostaglandin E1 derivatives and more particularly, misoprostol have been found to mitigate or provide protection against such ulcerogenic effects when co-administered with an NSAID.

Chemical degradation of certain prostaglandin type compounds, particularly prostaglandin E1 derivatives such as misoprostol, is accelerated in the presence of water, and the primary pathway of degradation is believed to be dehydration to the corresponding prostaglandin A derivative. The problem of chemical instability becomes more acute when the prostaglandin type compound is co formulated with certain NSAIDs such as diclofenac or piroxicam.

The present invention addresses and overcomes these commonly encountered problems.

SUMMARY OF THE INVENTION

In one general aspect there is provided a tablet dosage form. The dosage form includes a layer that includes a tablet of one or more active pharmaceutical ingredients, which is inlayed in the first layer along with other pharmaceutically acceptable excipients, and a second layer that includes one or more active pharmaceutical ingredients optionally with other pharmaceutically acceptable excipients.

The dosage form may include a coating. The tablet may be coated with one or more enteric polymers; pharmaceutically acceptable seal coat polymers or rate controlling polymers. The tablet may form a bilayered tablet.

The term "active ingredient" refers to a therapeutically active compound, as well as any prodrugs thereof and pharmaceutically acceptable salts, hydrates and solvates of the compound and the prodrugs.

The pharmaceutically acceptable excipients may include one or more of binders, fillers, antioxidants, disintegrants, surfactants, lubricants and glidants and the like.

In another general aspect there is provided a process of making dosage form. The dosage form may be made by a comprising of compressing a) first layer comprising of tablets of one or more active pharmaceutical ingredients with inert pharmaceutically acceptable excipients; and b) the second layer comprising of one or more active pharmaceutical ingredients along with inert pharmaceutically acceptable excipients into bilayered tablet dosage form.

In another general aspect there is provided a tablet dosage form. The dosage form includes a layer that includes a tablet of diclofenac or a salt thereof, wherein the tablet is inlayed in said layer with other pharmaceutically acceptable excipients and another layer that includes misoprostol or a salt thereof and optionally other pharmaceutically acceptable excipients.

The term "inlayed in said layer" is used herein to mean that the tablet of diclofenac or a salt thereof may be present at any position in said layer.

Embodiments of the dosage form may include one or more of the following features. For example, the dosage form may exhibit a dissolution profile such that within first 2 hours less than 2% of diclofenac or a salt thereof is released when the release rate is measured in Apparatus 2 (USP, Dissolution, paddle, 50 rpm) using 900 ml of 0.1N HCl at 37° C.±0.5° C. and within first 30 minutes more than 75% of diclofenac or a salt thereof is released, when the release rate is measured in Apparatus 2 (USP, Dissolution, paddle, 50 rpm) using 900 ml of pH 6.8 phosphate buffer at 37° C.±0.5° C.

The dosage form may include a coating. The tablet may be coated with one or more enteric polymers or pharmaceutically acceptable seal coat polymers. The tablet may form a bilayered tablet.

The pharmaceutically acceptable excipients may include one or more of binders, fillers, antioxidants, disintegrants, surfactants, lubricants and glidants and the like.

The details of one or more embodiments of the inventions are set forth in the description below. Other features, objects and advantages of the inventions will be apparent from the description and claims.

DESCRIPTION OF THE DRAWINGS

FIG. 1G shows an example of tablet dosage form of the invention.

FIG. 1H shows an example of tablet dosage form of the invention.

FIG. 1I shows an example of tablet dosage form of the invention.

DETAILED DESCRIPTION OF THE INVENTION

Figure 1A:
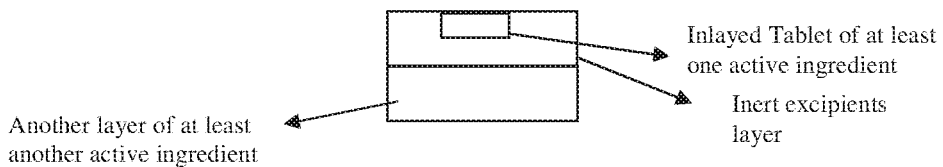
FIG. 1A shows example of tablet dosage form of the invention.
Figure 1B:
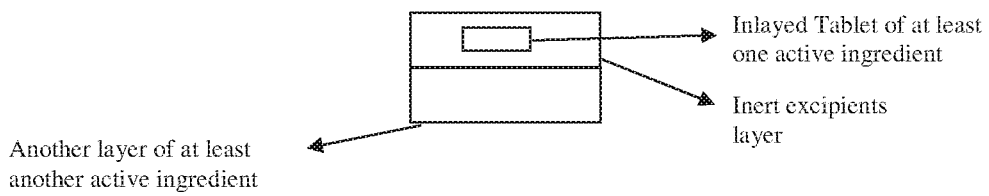
FIG. 1B shows an example of tablet dosage form of the invention.
Figure 1C:
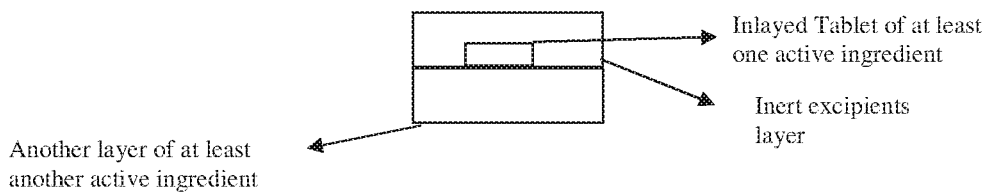
FIG. 1C shows an example of tablet dosage form of the invention.
Figure 1D:
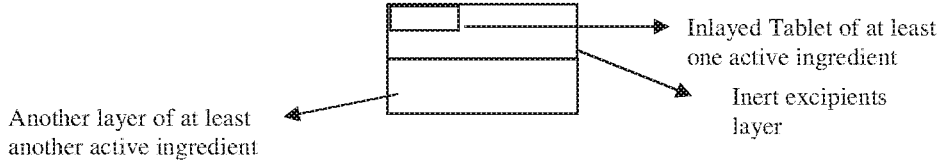
FIG. 1D shows an example of tablet dosage form of the invention.
Figure 1E:
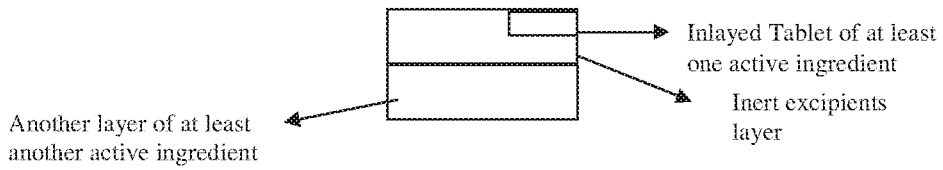
FIG. 1E shows an example of tablet dosage form of the invention.
Figure 1F:
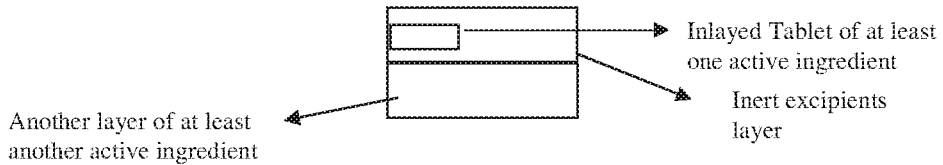
FIG. 1F shows an example of tablet dosage form of the invention.

As described above with respect to the difficulties associated with different classes of pharmaceutical active ingredients, which pose stability issues when present in a single unit system, there exists a need for universally applicable, unit dosage form or system. These difficulties are believed to be addressed by the techniques and concepts described herein. The present inventors have now discovered a novel tablet dosage form, which prevents a direct contact of one active ingredient with another ingredient thus leading to a stable system. The dosage form includes a first layer that includes a tablet of one or more active pharmaceutical ingredients, which is inlayed in the first layer along with inert pharmaceutically acceptable excipients, and a second layer that includes one or more active pharmaceutical ingredients optionally with other pharmaceutically acceptable excipients.

The inventors have now discovered that when misoprostol is not in a direct contact with diclofenac and outer environmental conditions, misoprostol is not degraded and a stable formulation can be prepared. According to one embodiment, when diclofenac tablet is inlayed in one layer along with inert pharmaceutically acceptable excipients, it is not in direct contact with misoprostol, which is present in another layer. Hence, misoprostol is prevented from degradation.

The inlayed tablet may be prepared by mixing at least one active ingredient optionally with other inert pharmaceutically acceptable excipients to form a premix, optionally converting the premix into granules and compressing the premix or granules into tablets. The inlayed tablet may include a coating. The tablet may be coated with one or more enteric polymers, pharmaceutically acceptable seal coat polymers or rate controlling polymers.

The one or more active pharmaceutical ingredients may be one or more of anti-inflammatory agents, sedatives, hypnotics, antibiotics, antidiabetics, antihypertensives, anti-osteoporosis agents, antithrombotic agents, antivirals, antifungals, anticholinergic agents, anxiolytic agents, adrenergics, antipsychotics, anti-parkinsonism agents, anticonvulsants, antiepileptics, CNS stimulants, antianginal agents, antiarrhythmics, antihyperlipidemic drugs, diuretics, antiasthmatics, anticoagulants, antianemia agents, vitamins, hormones, antihistaminics, anticancer agents, antiallergics, antiarthritis agents, antialzheimers' agents, vasopressin antagonists, anticonvulsants, steroids, anesthetics, thrombolytics, antacids, proton pump inhibitors, protease inhibitors, platelet aggregation inhibitors, mucolytics, antimalarials, antiemetics, laxatives, expectorants, enzymes, contraceptives, bronchodilators, antitussives, antimigraine agents, anthelmintics, and anorexiants.

The one or more active pharmaceutical ingredients may be one or more of amlodipine, diazepam, paracetamol, aspirin, ciprofloxacin, dicyclomine, celecoxib, alendronate, diacerein, acyclovir, fluconazole, epinephrine, divalproex, methylphenidate, flecainide, metoprolol, fenofibrate, hydrochlorothiazide, montelukast, heparin, warfarin, hemoglobin, iron, ascorbic acid, leutinizing hormone, bicalutamide, donepezil, tolvaptan, cortisones, lidocaine, calcium carbonate, saquinavir, bromhexine, promethazine, bisacodyl, pancreatin, ethinyl estradiol, salbutamol, diphenhydramine, sumatriptan, diclofenac, metronidazole, orlistat, ibuprofen, indomethacin, ketorolac, tramadolol, oxcarbazepine, pioglitazone, rosiglitazone, miglitol, vildagliptin, sitagliptin, repaglinide, voglibose, alprazolam, chlorpromazine, cimetidine, pseudoephedrine, naproxen, piroxicam, atenolol, benazepril, captopril, lisinopril, fosinopril, enalapril, furosemide, indapamide, atenolol, felodipine, verapamil, cartenolol, carvedilol, cerivastatin, diltiazem, fluvastatin, irbesartan, candesartan, methyldopa, reserpine, bupropion, fluoxetine, paroxetine, escitalopram, sertraline, amitryptiline, imipramine, fexofenadine, clopidogrel, entacapone, levodopa, carbidopa, levetiracetam, venlafaxine, duloxetine, lisinopril, losartan, lovastatin, niacin, pravastatin, ramipril, simvastatin, atorvastatin, valsartan, telmisartan, sildenafil, tadalafil, vardenafil, esomeprazole, famotidine, omeprazole, pantoprazole, rabeprazole, ranitidine, simethicone, artesunate, amodiaquine, benazepril, misoprostol, metformin, glipizide, and their pharmaceutically acceptable salts.

The active ingredient present in one or both layers of the dosage form may be present in an immediate release, delayed release, sustained release, extended release, controlled release or modified release form.

In general, one or both layers may include one or more rate controlling polymers. Suitable rate controlling polymers may include one or more of hydrophilic or hydrophobic polymers such as polyvinyl acetate, cellulose acetate, cellulose acetate butyrate, cellulose acetate propionate, ethyl cellulose, a fatty acid, a fatty acid ester, an alkyl alcohol, a wax, shellac, rosin, zein (prolamine from corn), a poly(meth)acrylate, microcrystalline cellulose or poly(ethylene oxide), polyuronic acid salts, cellulose ethers, xanthan gum, tragacanth gum, gum karaya, guar gum, acacia, gellan gum locust bean gum, alkali metal salts of alginic acid or pectic acid, sodium alginate, potassium alginate, ammonium alginate, hydroxypropyl cellulose, hydroxypropyl methylcellulose, carboxyvinyl polymers, and the like.

The dosage form of the present invention may be made by a comprising of compressing a) first layer comprising of tablets of one or more active pharmaceutical ingredients with inert pharmaceutically acceptable excipients; and b) the second layer comprising of one or more active pharmaceutical ingredients along with inert pharmaceutically acceptable excipients into bilayered tablet dosage form.

In one embodiment, diclofenac and misoprostol dosage form may be prepared by compressing tablets of diclofenac or a salt thereof and the misoprostol blend in such a way that the tablets of diclofenac or a salt thereof is inlayed at any position in one layer with other pharmaceutically acceptable excipients and misoprostol blend is compressed in another layer resulting in a bilayered tablet dosage form.

The tablets of diclofenac or a salt thereof may be prepared by mixing diclofenac or a salt thereof optionally with other pharmaceutically acceptable excipients to form a premix, optionally converting the premix into granules by dry granulation or wet granulation and compressing the premix or granules into tablets. Further, this tablet may optionally be coated with a seal coat polymer followed by enteric coating with pharmaceutically acceptable enteric coating polymers.

One layer of the diclofenac misoprostol tablet of the invention includes a diclofenac tablet inlayed at any position in said layer along with other pharmaceutically acceptable excipients and other layer includes misoprostol polymer dispersion in a mixture with other pharmaceutically acceptable excipients.

The polymer in the misoprostol-polymer dispersion may be one or more of hydroxypropyl methylcellulose, hydroxypropylcellulose, polyvinylpyrrolidone, and the like.

Suitable pharmaceutically acceptable seal coat polymers may include one or more of hydroxypropyl methylcellulose, hydroxypropyl cellulose and other suitable cellulose ethers.

Suitable pharmaceutically acceptable enteric coating polymers may include one or more of methacrylic acid/methyl methacrylate copolymers such as Eudragits or cellulose derivatives such as carboxymethyl cellulose, cellulose acetate phthalate, hydroxypropylmethyl cellulose phthalate, and other suitable polymers.

The dosage forms as described herein may include other pharmaceutically acceptable excipients. Examples of other pharmaceutically acceptable as used herein may include binders, fillers, antioxidants, disintegrants, surfactants, lubricants and glidants.

Suitable binders may include one or more of, povidone, starch, stearic acid, gums, hydroxypropylmethyl cellulose, and the like.

Suitable fillers may include one or more of, microcrystalline cellulose, lactose, mannitol, calcium phosphate, calcium sulfate, kaolin, dry starch, powdered sugar, and the like.

Suitable antioxidants may include one or more of dibutylhydroxy toluene (BHT), propyl gallate, butylhydroxyanisole (BHA), α-tocopherol, citric acid, and the like.

Suitable disintegrants may include one or more of starch, croscarmellose sodium, crospovidone, sodium starch glycolate, and the like.

Suitable surfactants may be anionic, non-ionic or cationic and may include one or more of polyoxyethylene hardened castor oil, glycerin monostearate, sorbitan monostearate, sorbitan monopalmitate, sorbitan monolaurate, a polyoxyethylene polyoxypropylene block copolymer, polysorbates, sodium lauryl sulfate, macrogols, sucrose fatty acid ester, and the like.

Suitable lubricants may include one or more of magnesium stearate, zinc stearate, calcium stearate, stearic acid, sodium stearyl fumarate, hydrogenated vegetable oil, and the like.

Suitable glidants may include one or more of colloidal silicon dioxide, talc or cornstarch, and the like.

While the present invention has been described in terms of its specific embodiments, certain modifications and equivalents will be apparent to those skilled in the art and are intended to be included within the scope of the present invention.

EXAMPLE 1

TABLE 1

| No | Ingredients | % Composition |
|---|---|---|
| | Misoprostol blend layer | |
| | Misoprostol:hypromellose (1:100) | |
| 1 | Misoprostol | 0.01 to 2.0 |
| 2 | Hypromellose | 10 to 99 |
| 3 | Crospovidone | 1 to 10 |
| 4 | Colloidal silicon dioxide | 0.1 to 10 |
| 5 | Microcrystalline cellulose | 10 to 90 |
| 6 | Hydrogenated castor oil | 0.1 to 2.0 |
| | Diclofenac sodium tablets in inert excipients layer | |
| 7 | Diclofenac sodium | 5 to 70 |
| 8 | Microcrystalline cellulose | 10 to 90 |
| 9 | Lactose | 10 to 90 |
| 10 | Sodium starch glycolate | 1 to 10 |
| 11 | Povidone | 1 to 10 |
| 12 | Magnesium stearate | 0.1 to 5 |
| | Seal coating | |
| 13 | Hypromellose + PEG 400 | 1 to 5 |
| 14 | Purified water | q. s. |
| | Enteric coating | |
| 15 | Methacrylic acid copolymer suspension (Methacrylic acid copolymer, sodium hydroxide, Talc, triethyl citrate, purified water) | 8 to 25 |
| | Inert excipients | |
| 16 | Crospovidone | 1 to 10 |
| 17 | Microcrystalline cellulose | 10 to 80 |
| 18 | Colloidal silicon dioxide | 0.1 to 10 |
| 19 | Hydrogenated castor oil | 0.1 to 2.0 |

Procedure: Misoprostol-hypromellose dispersion was mixed with microcrystalline cellulose, crospovidone, and colloidal silicon dioxide in a double cone blender. The above mixture was lubricated with pre-sifted hydrogenated castor oil in a double cone blender to form the misoprostol blend.

Diclofenac sodium was mixed with microcrystalline cellulose, lactose, povidone, and sodium starch glycollate in a double cone blender to form a pre-mix. The pre-mix was further mixed with povidone and converted into flakes by compacting it through a roll compactor. The flakes were sized into granules, which were then lubricated with magnesium stearate in a double cone blender, and the lubricated granules were compressed into tablets using a suitable tooling.

The compressed tablets were further seal coated with hypromellose polyethylene glycol solution in water. The seal coated diclofenac sodium tablets were coated with enteric polymer suspension prepared by mixing methacrylic acid polymer, sodium hydroxide, talc, triethyl citrate in water. Inert excipients like crospovidone, colloidal silicon dioxide, sodium starch glycollate, microcrystalline cellulose and hydrogenated castor oil were mixed together in a double cone blender.

The enteric-coated diclofenac sodium tablets were compressed along with inert excipients and the misoprostol blend in such a way that diclofenac sodium tablet was inlayed at any position in the first layer along with inert excipients and the misoprostol blend was compressed as a second layer to form a bilayered tablet dosage form. Finally, the bilayered tablet was further coated with an aqueous dispersion of Opadry.

EXAMPLE 2

TABLE 2

| No | Ingredients | % Composition |
|---|---|---|
| | Benazepril blend layer | |
| 1 | Benazepril | 0.5 to 25 |
| 2 | Calcium phosphate dibasic | 10 to 99 |
| 3 | Crospovidone | 1 to 10 |
| 4 | Colloidal silicon dioxide | 0.1 to 10 |
| 5 | Microcrystalline cellulose | 10 to 90 |
| 6 | Talc | 0.1 to 2.0 |
| | Amlodipine tablets in inert excipients layer | |
| 7 | Amlodipine | 0.01 to 4.0 |
| 8 | Microcrystalline cellulose | 10 to 90 |
| 9 | Lactose | 10 to 90 |
| 10 | Pregelatinized starch | 1 to 10 |
| 11 | Crospovidone | 1 to 10 |
| 12 | Magnesium stearate | 0.1 to 5 |
| | Inert excipients | |
| 13 | Crospovidone | 1 to 10 |
| 14 | Microcrystalline cellulose | 10 to 80 |
| 15 | Colloidal silicon dioxide | 0.1 to 10 |
| 16 | Hydrogenated castor oil | 0.1 to 2.0 |

Procedure: Benazepril was mixed with microcrystalline cellulose, crospovidone, and colloidal silicon dioxide in a suitable blender. The above mixture was lubricated with talc in a suitable blender to form the benazepril blend.

Amlodipine was mixed with microcrystalline cellulose, lactose, pregelatinized starch, in a suitable blender to form a pre-mix. The pre-mix was further mixed with crospovidone and converted into flakes by compacting it through a suitable compactor. The flakes were sized into granules, which were then lubricated with magnesium stearate in a suitable blender, and the lubricated granules were compressed into tablets using a suitable tooling.

Inert excipients like crospovidone, colloidal silicon dioxide, sodium starch glycollate, microcrystalline cellulose and hydrogenated castor oil were mixed together in a suitable blender.

The amlodipine tablets were compressed along with inert excipients and benazepril blend in such a way that the amlodipine tablet was inlayed at any position in the first layer along with inert excipients and the benazepril blend was compressed as a second layer to form a bilayered tablet dosage form.

EXAMPLE 3

TABLE 3

| No | Ingredients | % Composition |
|---|---|---|
| | Telmisartan blend layer | |
| 1 | Telmisartan | 0.1 to 20.0 |
| 2 | Hydroxy propyl cellulose | 10 to 99 |
| 3 | Crospovidone | 1 to 10 |
| 4 | Colloidal silicon dioxide | 0.1 to 10 |
| 5 | Microcrystalline cellulose | 10 to 90 |
| 6 | Magnesium stearate | 0.1 to 2.0 |
| | Amlodipine tablets in inert excipients layer | |
| 7 | Amlodipine | 0.01 to 4.0 |
| 8 | Microcrystalline cellulose | 10 to 90 |
| 9 | Lactose | 10 to 90 |
| 10 | Pregelatinized starch | 1 to 10 |
| 11 | Crospovidone | 1 to 10 |
| 12 | Magnesium stearate | 0.1 to 5 |
| | Inert excipients | |
| 13 | Crospovidone | 1 to 10 |
| 14 | Microcrystalline cellulose | 10 to 80 |
| 15 | Colloidal silicon dioxide | 0.1 to 10 |
| 16 | Hydrogenated castor oil | 0.1 to 2.0 |

Procedure: Telmisartan was mixed with microcrystalline cellulose, crospovidone, and colloidal silicon dioxide in a suitable blender. The above mixture was lubricated with talc in a suitable blender to form the telmisartan blend.

Amlodipine was mixed with microcrystalline cellulose, lactose, pregelatinized starch, in a suitable blender to form a pre-mix. The pre-mix was further mixed with crospovidone and converted into flakes by compacting it through a suitable compactor. The flakes were sized into granules, which were then lubricated with magnesium stearate in a suitable blender, and the lubricated granules were compressed into tablets using a suitable tooling.

Inert excipients like crospovidone, colloidal silicon dioxide, sodium starch glycollate, microcrystalline cellulose and hydrogenated castor oil were mixed together in a suitable blender.

The amlodipine tablets were compressed along with inert excipients and the telmisartan blend in such a way that the amlodipine tablet was inlayed at any position in the first layer along with inert excipients and the telmisartan blend was compressed as a second layer to form a bilayered tablet dosage form.

EXAMPLE 4

TABLE 4

| No | Ingredients | % Composition |
|---|---|---|
| | Atorvastatin blend layer | |
| 1 | Atorvastatin | 0.1 to 20.0 |
| 2 | Calcium carbonate | 1 to 10 |
| 3 | Croscarmellose sodium | 1 to 10 |

TABLE 4-continued

| No | Ingredients | % Composition |
|---|---|---|
| 4 | Colloidal silicon dioxide | 0.1 to 10 |
| 5 | Microcrystalline cellulose | 10 to 90 |
| 6 | Magnesium stearate | 0.1 to 2.0 |
| | Amlodipine tablets in inert excipients layer | |
| 7 | Amlodipine | 0.01 to 4.0 |
| 8 | Microcrystalline cellulose | 10 to 90 |
| 9 | Lactose | 10 to 90 |
| 10 | Pregelatinized starch | 1 to 10 |
| 11 | Crospovidone | 1 to 10 |
| 12 | Magnesium stearate | 0.1 to 5 |
| | Inert excipients | |
| 13 | Crospovidone | 1 to 10 |
| 14 | Microcrystalline cellulose | 10 to 80 |
| 15 | Colloidal silicon dioxide | 0.1 to 10 |
| 16 | Hydrogenated castor oil | 0.1 to 2.0 |

Procedure: Atorvastatin was mixed with microcrystalline cellulose, crospovidone, and colloidal silicon dioxide in a suitable blender. The above mixture was lubricated with talc in a suitable blender to form the atorvastatin blend.

Amlodipine was mixed with microcrystalline cellulose, lactose, pregelatinized starch, in a suitable blender to form a pre-mix. The pre-mix was further mixed with crospovidone and converted into flakes by compacting it through a suitable compactor. The flakes were sized into granules, which were then lubricated with magnesium stearate in a suitable blender, and the lubricated granules were compressed into tablets using a suitable tooling.

Inert excipients like crospovidone, colloidal silicon dioxide, sodium starch glycollate, microcrystalline cellulose and hydrogenated castor oil were mixed together in a suitable blender.

The amlodipine tablets were compressed along with inert excipients and the atorvastatin blend in such a way that the amlodipine tablet was inlayed at any position in the first layer along with inert excipients and the atorvastatin blend was compressed as a second layer to form a bilayered tablet dosage form.

While the invention has been described in terms of its specific embodiments, certain modifications and equivalents will be apparent to those skilled in the art and are intended to be included within the scope of the invention.

We claim:

1. A bilayered tablet dosage form comprising:
a first layer comprising one or more pharmaceutically acceptable inert excipients;
a second layer comprising one or more active pharmaceutical ingredients, one or more pharmaceutically acceptable excipients, and an inlaid tablet comprising the one or more active pharmaceutical ingredients, wherein the inlaid tablet is coated with a seal coating layer comprising one or more seal coat polymers followed by enteric coating with enteric polymer, and the inlaid tablet comprise diclofenac or salts thereof; and
wherein the dosage form comprises:

| No | Ingredients |
|---|---|
| | Active pharmaceutical ingredient layer |
| | Hypromellose |
| 2 | Crospovidone |
| 3 | Colloidal silicon dioxide |
| 4 | Microcrystalline cellulose |
| 5 | Hydrogenated castor oil |

| No | Ingredients |
|---|---|
| | Diclofenac sodium tablets in inert excipients layer |
| 6 | Microcrystalline cellulose |
| 7 | Lactose |
| 8 | Sodium starch glycolate |
| 9 | Povidone |
| 10 | Magnesium stearate |
| | Seal coating |
| 11 | Hypromellose + PEG 400 |
| 12 | Purified water |
| | Enteric coating |
| 13 | Methacrylic acid copolymer suspension (Methacrylic acid copolymer, sodium hydroxide, Talc, triethyl citrate, purified water) |
| | Inert excipients |
| 14 | Crospovidone |
| 15 | Microcrystalline cellulose |
| 16 | Colloidal silicon dioxide |
| 17 | Hydrogenated castor oil. |

2. The dosage form of claim 1, wherein the one or more active pharmaceutical ingredients is present in an immediate release, delayed release, sustained release, extended release, controlled release or modified release form.

3. The dosage form of claim 1, wherein the inlaid tablet is further coated with one or more rate controlling polymers.

4. The dosage form of claim 3, wherein the rate-controlling polymer comprises one or more of hydrophilic and hydrophobic polymers.

5. The dosage form of claim 4, wherein the hydrophilic or hydrophobic polymer comprises one or more of polyvinyl acetate, cellulose acetate, cellulose acetate butyrate, cellulose acetate propionate, ethyl cellulose, a fatty acid, a fatty acid ester, an alkyl alcohol, a wax, shellac, rosin, zein (prolamine from corn), a poly(meth)acrylate, microcrystalline cellulose or poly(ethylene oxide), polyuronic acid salts, cellulose ethers, xanthan gum, tragacanth gum, gum karaya, guar gum, acacia, gellan gum locust bean gum, alkali metal salts of alginic acid or pectic acid, sodium alginate, potassium alginate, ammonium alginate, hydroxypropyl cellulose, hydroxypropyl methylcellulose, and carboxyvinyl polymers.

6. The dosage form of claim 1, further comprising one or more active pharmaceutical ingredients selected from amlodipine, diazepam, paracetamol, aspirin, ciprofloxacin, dicyclomine, celecoxib, alendronate, diacerein, acyclovir, fluconazole, epinephrine, divalproex, methylphenidate, flecainide, metoprolol, fenofibrate, hydrochlorothiazide, montelukast, heparin, warfarin, hemoglobin, iron, ascorbic acid, leutinizing hormone, bicalutamide, donepezil, tolvaptan, cortisones, lidocaine, calcium carbonate, saquinavir, bromhexine, promethazine, bisacodyl, pancreatin, ethinyl estradiol, salbutamol, diphenhydramine, sumatriptan, diclofenac, metronidazole, orlistat, ibuprofen, indomethacin, ketorolac, tramadolol, oxcarbazepine, pioglitazone, rosiglitazone, miglitol, vildagliptin, sitagliptin, repaglinide, voglibose, alprazolam, chlorpromazine, cimetidine, pseudoephedrine, naproxen, piroxicam, atenolol, benazepril, captopril, lisinopril, fosinopril, enalapril, furosemide, indapamide, atenolol, felodipine, verapamil, cartenolol, carvedilol, cerivastatin, diltiazem, fluvastatin, irbesartan, candesartan, methyldopa, reserpine, bupropion, fluoxetine, paroxetine, escitalopram, sertraline, amitryptiline, imipramine, fexofenadine, clopidogrel, entacapone, levodopa, carbidopa, levetiracetam, venlafaxine, duloxetine, lisinopril, losartan, lovastatin, niacin, pravastatin, ramipril, simvastatin, atorvastatin, valsartan, telmisartan, sildenafil, tadalafil, vardenafil, esomeprazole, famotidine, omeprazole, pantoprazole, rabeprazole, ranitidine, simethicone, artesunate, amodiaquine, benazepril, misoprostol, metformin, glipizide, and their pharmaceutically acceptable salts.

7. The dosage form of claim 1, wherein the pharmaceutically acceptable excipients further comprising one or more of binders, fillers, antioxidants, disintegrants, surfactants, lubricants, and glidants.

8. A bilayered tablet dosage form comprising:
   a first layer comprising one or more pharmaceutically acceptable inert excipients;
   a second layer comprising misoprostol or a salt thereof and optionally other pharmaceutically acceptable excipients and
   an inlaid tablet comprising diclofenac or salts thereof along with one or more pharmaceutically acceptable excipients; wherein the inlaid tablet of diclofenac or salt thereof is coated with a pharmaceutically acceptable seal coating layer comprising one or more seal coated polymers followed by enteric coating with enteric polymer:
   wherein the dosage form exhibits a dissolution profile such that within first 2 hours less than 2% of the diclofenac or salt thereof is released when the release rate is measured in Apparatus 2 (USP, Dissolution, paddle, 50 rpm) using 900 ml of 0.1N HCl at 37° C. ±0.5°C. and within first 30 minutes more than 75% of the diclofenac or salt thereof is released when the release rate is measured in Apparatus 2 (USP, Dissolution, paddle, 50 rpm) using 900 ml of pH 6.8 phosphate buffer at 37° C. ±0.5° C; wherein the inlaid tablet contains 5 to 70% of diclofenac or salt thereof; and wherein the dosage form comprises:

| No | Ingredients |
| --- | --- |
| Active pharmaceutical ingredient layer | |
| 1 | Hypromellose |
| 2 | Crospovidone |
| 3 | Colloidal silicon dioxide |
| 4 | Microcrystalline cellulose |
| 5 | Hydrogenated castor oil |
| Diclofenac sodium tablets in inert excipients layer | |
| 6 | Microcrystalline cellulose |
| 7 | Lactose |
| 8 | Sodium starch glycolate |
| 9 | Povidone |
| 10 | Magnesium stearate |
| Seal coating | |
| 11 | Hypromellose + PEG 400 |
| 12 | Purified water |
| Enteric coating | |
| 13 | Methacrylic acid copolymer suspension (Methacrylic acid copolymer sodium hydroxide, Talc, triethyl citrate, purified water) |
| Inert excipients | |
| 14 | Crospovidone |
| 15 | Microcrystalline cellulose |
| 16 | Colloidal silicon dioxide |
| 17 | Hydrogenated castor oil. |

9. A process of preparing a bilayered tablet dosage form of claim 1, wherein the process comprises compressing
   a. a first layer comprising tablet(s) of one or more active pharmaceutical ingredients, wherein the tablet(s) is/are inlayed in the first layer along with inert pharmaceutically acceptable excipients; and
   b. a second layer comprising one or more active pharmaceutical ingredients along with inert pharmaceutically acceptable excipients,
into a bilayered tablet dosage form, wherein the inlaid tablet(s) is/are coated with a seal coating layer comprising one or more seal coat polymers followed by enteric coating with enteric polymer.

* * * * *